US011883596B1

(12) United States Patent
Paulsen

(10) Patent No.: US 11,883,596 B1
(45) Date of Patent: Jan. 30, 2024

(54) ORAL PHARYNGEAL AIRWAY

(71) Applicant: Heath Paulsen, Polk City, IA (US)

(72) Inventor: Heath Paulsen, Polk City, IA (US)

( * ) Notice: Subject to any disclaimer, the term of this patent is extended or adjusted under 35 U.S.C. 154(b) by 271 days.

(21) Appl. No.: 16/893,582

(22) Filed: Jun. 5, 2020

Related U.S. Application Data

(60) Provisional application No. 62/857,339, filed on Jun. 5, 2019.

(51) Int. Cl.
*A61M 16/04* (2006.01)
*A61M 16/06* (2006.01)

(52) U.S. Cl.
CPC .... *A61M 16/0463* (2013.01); *A61M 16/0666* (2013.01)

(58) Field of Classification Search
CPC ...................... A61M 16/0683; A61M 16/0666
USPC ..................................................... 128/207.14
See application file for complete search history.

(56) References Cited

U.S. PATENT DOCUMENTS 3,576,187 A * 4/1971 Oddera ............ A61M 16/0488 128/207.14
3,867,946 A * 2/1975 Huddy ............. A61M 16/0666 128/207.18
3,908,665 A * 9/1975 Moses .................... A61B 1/267 128/207.14
4,054,135 A * 10/1977 Berman ........... A61M 16/0493 128/207.14
4,270,531 A * 6/1981 Blachly ............ A61M 16/0495 128/207.14
8,820,320 B2 * 9/2014 Filipi ............... A61M 16/0495 128/200.26
9,254,219 B2 * 2/2016 Shantha .................. A61F 5/566
10,286,172 B1 * 5/2019 Schmidt ........... A61M 16/0431
2004/0102711 A1 * 5/2004 Wall .................... B29C 45/1704 600/532
2005/0139220 A1 * 6/2005 Christopher .......... A61M 16/04 128/207.14
2009/0013995 A1 * 1/2009 Williams ............ A61M 16/085 128/207.14
2010/0065062 A1 * 3/2010 Rajan ............... A61M 16/0484 128/207.14
2011/0168188 A1 * 7/2011 Moore ............. A61M 16/0495 128/848

* cited by examiner

*Primary Examiner* — Craig M Schneider
*Assistant Examiner* — David R Deal
(74) *Attorney, Agent, or Firm* — David L. Principe; Phillips Lytle LLP

(57) ABSTRACT

An improved oral pharyngeal airway for suction and delivery of oxygen to a patient during medical procedures.

4 Claims, 4 Drawing Sheets

40
37
27
34
37
19

ORAL PHARYNGEAL AIRWAY

CROSS-REFERENCE TO RELATED APPLICATION

The present application claims priority benefit of U.S. Provisional Patent Application No. 62/857,339 filed Jun. 5, 2019, entitled "Oral Pharyngeal Airway," which is incorporated herein by reference.

BACKGROUND ART

An oropharyngeal airway (OPA), also referred to as an oral airway, is used to create an air passageway between the mouth and the posterior pharyngeal wall of a patient. Unconscious patients (e.g., under general anesthesia) and heavily sedated semi-unconscious patients (e.g., under monitored anesthesia care (MAC)) may have an oral airway inserted to relieve an obstructed airflow. There are two main airways used today—The Berman Airway and Guedal Airway. These products keep the airway open in the pharynx area. Secretions can cause obstructions of the airway. Therefore, other devices need to be used along with the oral airways. These include the Yankuer suction tip and also the flexible suction catheter. With the airway open and the patient sedated, supplemental oxygen is often used to keep oxygen saturations stable during hypoventilation (decreased breathing). Oral cannula and nasal cannula may be used to achieve this. Products on the mark require additional resources and do not function independently. As a result of the limitations of the existing products, the patient either compensates or deteriorates quickly. Previous attempts at manufacturing oral pharyngeal airways have resulted in expensive devices with multiple molded parts that can fall apart into the airway. Also, these products restrict practitioners from using conventional methods and products in connection with the airway. These limitations hinder the life saving, medical treatment time and may result in poor outcomes. What is needed is an oral pharyngeal airway that is designed to easily adapt to varying suction and oxygen needs of a patient.

SUMMARY OF THE INVENTION

The present invention meets the above described need by providing an oral pharyngeal airway for use with a nasal cannula. The airway comprises an elongate body having a proximal end and a distal end. A first section terminates at the proximal end and a second arcuate section terminates at the distal end. The elongate body has a central opening disposed in fluid communication with a longitudinal passageway formed therein. The longitudinal passageway extends between the proximal end and the distal end.

A pair of spaced apart longitudinal flanges extend along the length of the body to form an elongate channel therebetween. The channel is configured to provide an additional passageway.

A universal port is disposed adjacent the proximal end of the body and surrounds the central opening.

The longitudinal flanges are configured to hold the nasal cannula in place on the universal port.

In another aspect of the invention, additional openings are disposed in fluid communication with the longitudinal passageway. The additional openings surround the central opening at the distal end of the body.

In another aspect of the invention, a side opening is disposed in fluid communication with the longitudinal passageway. The side opening has a diameter smaller than the central opening at the distal end.

DESCRIPTION OF THE PREFERRED EMBODIMENTS

Figure 1:
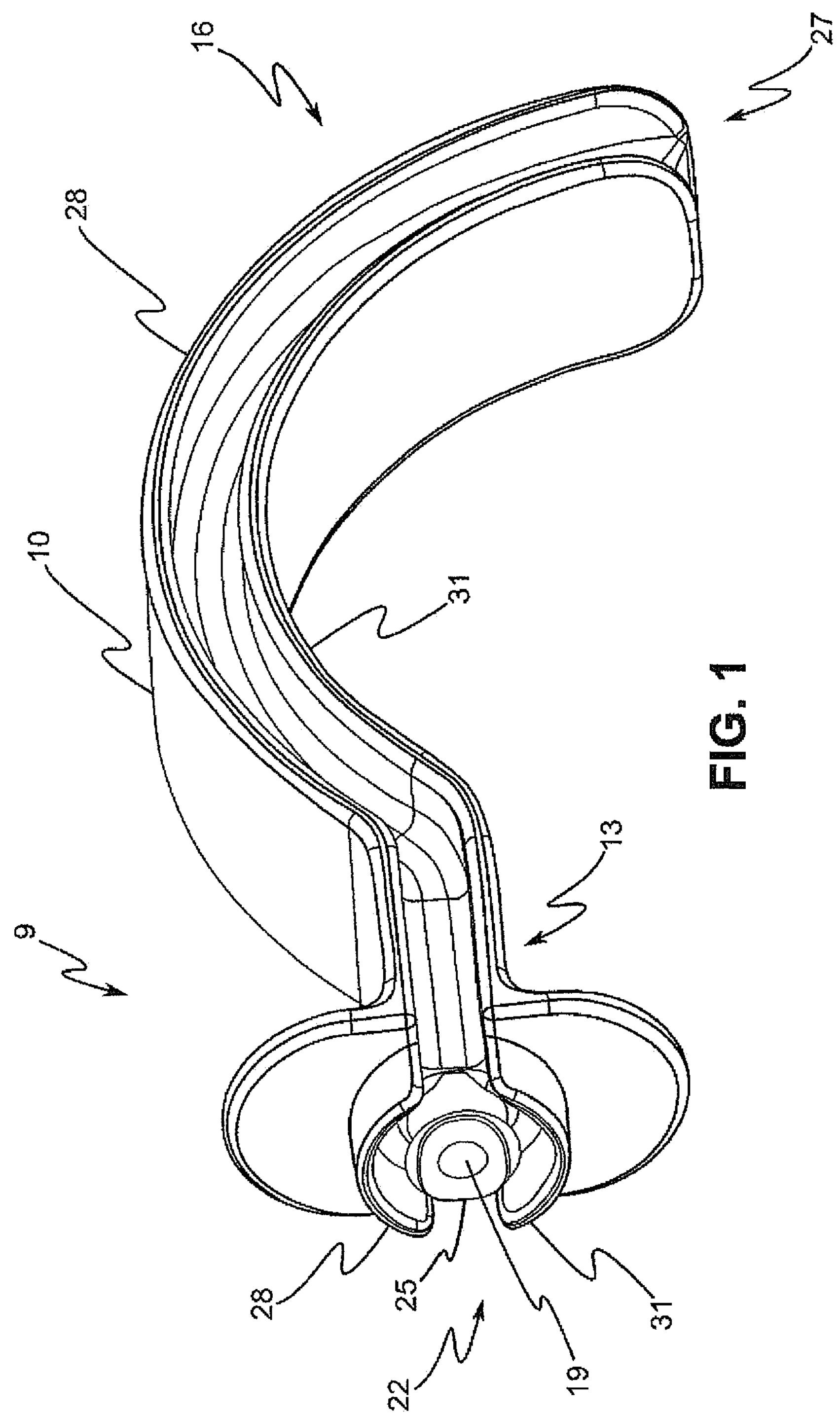
FIG. 1 is a perspective view of a first embodiment of the oral pharyngeal airway of the present invention.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Referring now to the drawings, and more particularly to FIG. 1 thereof, this invention provides an oral pharyngeal airway 9 having an elongate body 10 formed of a suitable rigid material that may be injection molded for example. The body 10 includes a proximal straight section 13 and a distal arcuate section 16. The body 10 has a longitudinal opening 19 terminating at the proximate end 22. The longitudinal opening 19 is surrounded by a universal port 25. A pair of spaced apart flanges 28, 31 may be disposed around the universal port 25 and may extend in spaced apart relation from the proximal end 22 to the distal end 27 of the airway 9. The flanges 28 and 31 provide an additional passageway on each, side for breathing gases for the patient. The portion of the flanges 28, 31 surrounding the universal port 25 provide a friction fit for connection to an anesthesia circuit. The surface between the flanges 28, 31 and the universal port 25 may be recessed to allow the universal port 25 to fit deeper into suction or oxygen tubing connected to the port 25. The flanges 28, 31 also hold a nasal cannula in place on the universal port 25.

On the suction requirement—the airway 9 hooks up to standard suction tubing but also allows for traditional uses of yankeur and flexible suction tubing. For the oxygen requirement—the airway 9 hooks up to standard oxygen tubing, nasal cannula (orally and nasally), and an oxygen mask. This configuration allows for oxygen to be given outside of the body or to be given just outside the larynxy (hypopharynx).

This flexibility allows practioners to adapt within seconds to provide what a patient needs. If the patient deteriorates while using a nasal cannula, the nasal cannula can still be used in the side flanges in the indentation near universal port 25. This allows practioners to still use the same resources that are available in any given situation.

Figure 2:
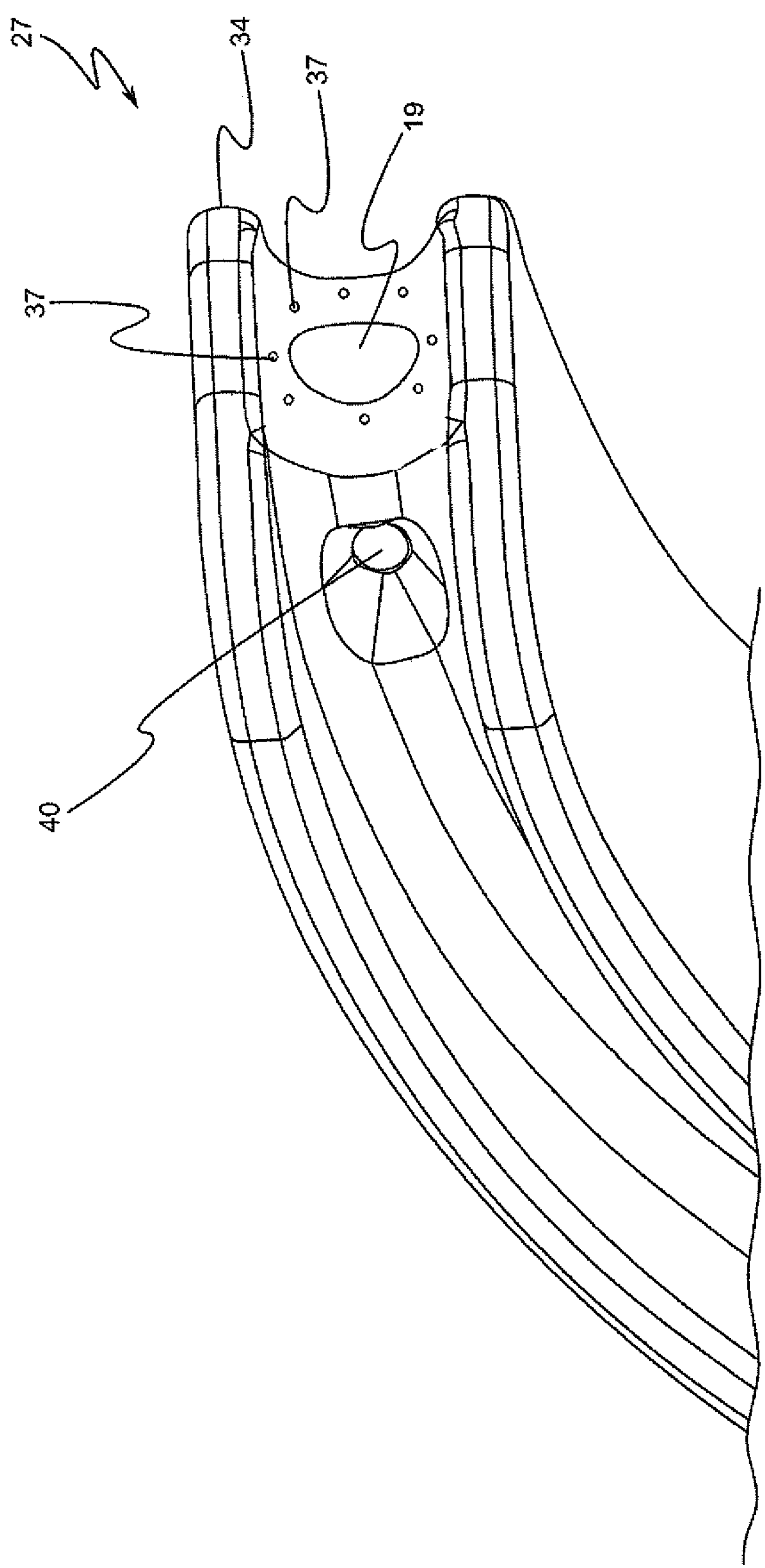
FIG. 2 is an enlarged perspective view of the distal end of the oral pharyngenal airway of the present invention.

Turning to FIG. 2, the distal end 27 of the oral airway 9 can either be configured with a distal tip 34 that extends beyond the flanges 28, 31 to allow for a deeper suction or it may be recessed concavely into the flanges 28, 31 as shown to prevent suctioning of soft tissue of the airway. The distal end 27 provides a termination point for longintudinal opening 19. The distal tip 34 may also include additional openings 37 surrounding longitudinal opening 19. In addition, a side opening 40 may be provided for pressure relief in the event that the longitudinal opening 19 becomes obstructed. The tapering of the surface around opening 40 provides for wider suctioning without taking suction power from longitudinal opening 19 at the distal end 27 of the airway 9.

The product will adapt to any situation. The universal port 25 on the proximal end 22 will for changes to be made on the fly for suction and oxygen. This device will help patients suction and oxygen reaction times, decrease medical expenses, and decrease the need for additional resources.

The distal resected suction tip 34 will prevent soft tissues injuries, which in return will allow the practitioner to provide higher suctioning pressures. This configuration is much more effective in clearing secretions out of the airway.

Figure 3:
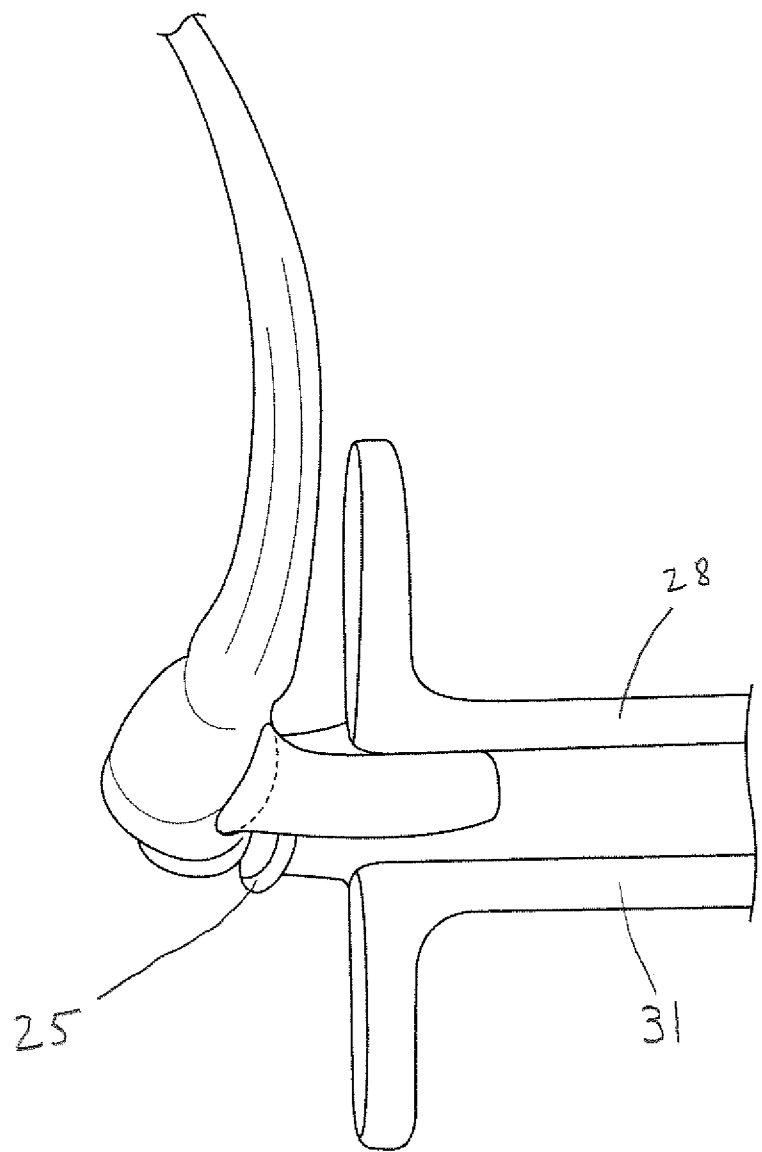
FIG. 3 is an enlarged side view showing the connection of a nasal cannula to the proximal end of the oral pharyngeal airway.
Figure 4:
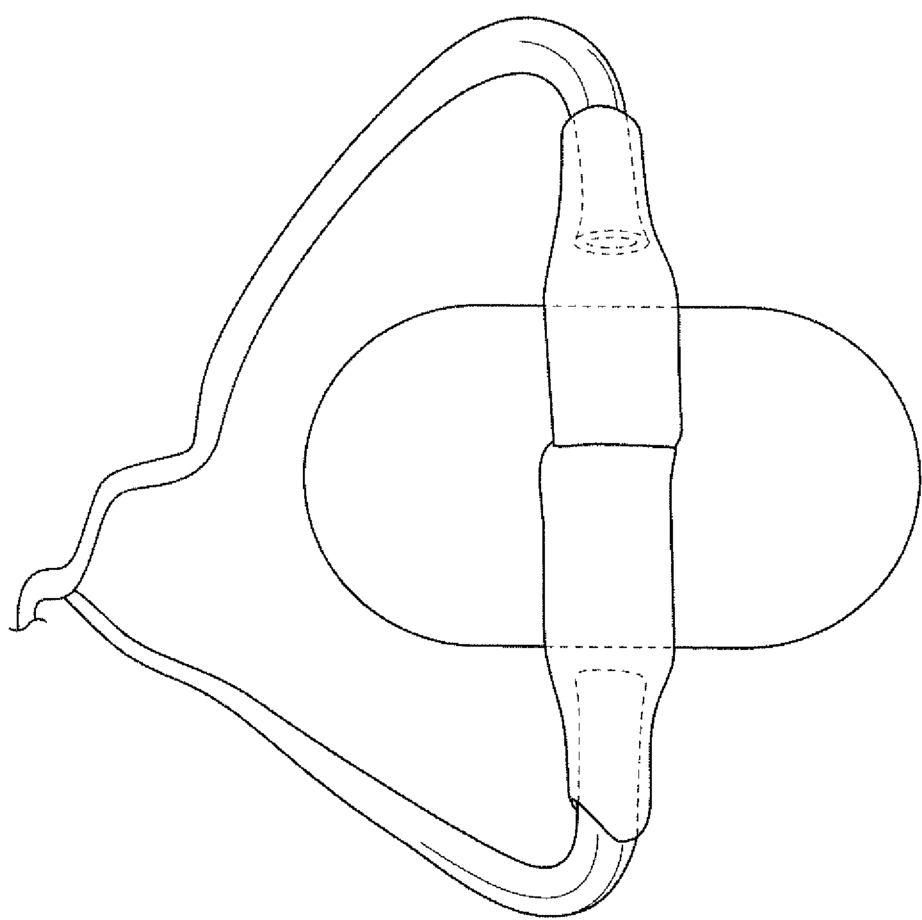
FIG. 4 is a front plan view showing the connection of a nasal cannula to the proximal end of the oral pharyngeal airway.

FIGS. 3 and 4 show the attachment of a nasal cannula to the proximate end 22 of the airway 9. For clarity, the flanges 28 and 31 are removed from the area around the universal port 25.

The present invention provides many advantages including providing a product that decreases suction/oxygen reaction time while allowing conventional methods.

The present invention contemplates that many changes and modifications may be made. Therefore, while the presently-preferred form of the oral pharyngeal airway has been shown and described, and several modifications and alternatives discussed, persons skilled in this art will readily appreciate that various additional changes and modifications may be made without departing from the spirit of the invention.

The invention claimed is:

1. An oral pharyngeal airway for use with a nasal cannula, the airway comprising:

an elongate body having a proximal end and a distal end, a first section terminates at the proximal end and a second arcuate section terminates at the distal end, the elongate body having a central opening disposed in fluid communication with a longitudinal passageway formed therein, the longitudinal passageway extending between the proximal end and the distal end;

a pair of spaced apart longitudinal flanges extending along the length of the body to form an elongate channel therebetween, the channel configured to provide an additional passageway;

a universal port disposed adjacent the proximal end of the body and surrounding the central opening; and, wherein the longitudinal flanges are configured to hold the nasal cannula in place on the universal port, further comprising additional openings in fluid communication with the longitudinal passageway, the additional openings surrounding the central opening at the distal end of the body.

2. An oral pharyngeal airway for use with a nasal cannula, the airway comprising:

an elongate body having a proximal end and a distal end, a first section terminates at the proximal end and a second arcuate section terminates at the distal end, the elongate body having a first central opening at the proximal end, the first central opening disposed in fluid communication with a longitudinal passageway formed therein, the elongate body having a second central opening at the distal end, the longitudinal passageway extending between the proximal end and the distal end;

a pair of spaced apart longitudinal flanges extending along the length of the body to form an elongate channel therebetween, the channel configured to provide an additional passageway;

a universal port disposed adjacent the proximal end of the body and surrounding the central opening; and, wherein the longitudinal flanges are configured to hold the nasal cannula in place on the universal port, and;

further comprising a side opening disposed in fluid communication with the longitudinal passageway, the side opening having a diameter smaller than the second central opening at the distal end, wherein the side opening is surrounded by a recessed portion extending inward from the outer surface of the elongate body such that the side opening is disposed inward in spaced apart relation to the outer surface of the elongate body.

3. An oral pharyngeal airway for use with a nasal cannula, the airway comprising:

an elongate body having a proximal end and a distal end, a first section terminates at the proximal end and a second arcuate section terminates at the distal end, the elongate body having a first central opening at the proximal end, the first central opening disposed in fluid communication with a longitudinal passageway formed therein, the elongate body having a second central opening at the distal end, the longitudinal passageway extending between the proximal end and the distal end;

a pair of spaced apart longitudinal flanges extending along the length of the body to form an elongate channel therebetween, the channel configured to provide an additional passageway;

a universal port disposed adjacent the proximal end of the body and surrounding the central opening; and, wherein the longitudinal flanges are configured to hold the nasal cannula in place on the universal port, and; wherein the second central opening is surrounded by a concave surface at the distal end.

4. An oral pharyngeal airway for use with a nasal cannula, the airway comprising:

an elongate body having a proximal end and a distal end, a first section terminates at the proximal end and a second arcuate section terminates at the distal end, the elongate body having a first central opening at the proximal end, the first central opening disposed in fluid communication with a longitudinal passageway formed therein, the elongate body having a second central opening at the distal end, the longitudinal passageway extending between the proximal end and the distal end;

a pair of spaced apart longitudinal flanges extending along the length of the body to form an elongate channel therebetween, the channel configured to provide an additional passageway;

a universal port disposed adjacent the proximal end of the body and surrounding the central opening; and, wherein the longitudinal flanges are configured to hold the nasal cannula in place on the universal port, and; wherein the second central opening is surrounded by a convex surface at the distal end.

* * * * *